(12) United States Patent
Rosman et al.

(10) Patent No.: US 9,327,284 B2
(45) Date of Patent: May 3, 2016

(54) SAMPLING AND ASSAY DEVICE (75) Inventors: Esa Rosman, Turku (FI); Anna Kaisa Kylmä, Luoma (FI); Veli-Mies Häivä, Espoo (FI); Christer Grandberg, Kirkkonummi (FI)

(73) Assignee: ORION DIAGNOSTICA OY, Espoo (FI)

( * ) Notice: Subject to any disclaimer, the term of this patent is extended or adjusted under 35 U.S.C. 154(b) by 569 days.

(21) Appl. No.: 10/586,697

(22) PCT Filed: Jan. 19, 2005

(86) PCT No.: PCT/EP2005/000484
§ 371 (c)(1),
(2), (4) Date: Jun. 25, 2008

(87) PCT Pub. No.: WO2005/071388
PCT Pub. Date: Aug. 4, 2005

(65) Prior Publication Data
US 2008/0260581 A1    Oct. 23, 2008

(30) Foreign Application Priority Data

Jan. 21, 2004   (GB) .................................. 0401288.6

(51) Int. Cl.
*B01L 3/00*     (2006.01)
*B65D 81/32*    (2006.01)
*G01N 1/02*     (2006.01)

(52) U.S. Cl.
CPC ........... *B01L 3/5029* (2013.01); *B65D 81/3211* (2013.01); *B01L 3/5082* (2013.01);
(Continued)

(58) Field of Classification Search
USPC ............ 422/58, 61, 68.1, 236, 512, 405, 406, 422/408, 413, 430; 435/7.34, 36, 91.2, 435/287.2, 287.6, 288.2, 288.5; 436/165, 8; 366/142; 137/14, 797; 73/64.56, 866
See application file for complete search history.

(56) References Cited

U.S. PATENT DOCUMENTS 4,067,440 A  *  1/1978  Lataix .......................... 206/222
4,353,868 A     10/1982  Joslin et al.
(Continued)

FOREIGN PATENT DOCUMENTS

EP        1 143 012 A1    10/2001
EP        1 167 968 A1     1/2002
(Continued)

OTHER PUBLICATIONS

IP Australia Office Action regarding Application No. 2005206628, dated Feb. 2, 2010.
(Continued)

*Primary Examiner* — Jill Warden
*Assistant Examiner* — Matthew Krcha
(74) *Attorney, Agent, or Firm* — Harness, Dickey & Pierce, P.L.C.

(57) ABSTRACT

A sampling and assay device comprises at least three chamber portions connected together in a row. Each chamber portion defines a chamber separated by respective partitions. One end chamber is capable of receiving a sample. The other chambers contain reagent. In respect of each pair of adjacent chamber portions one of the adjacent chamber portions has the respective partition fixed thereto and the other of the adjacent chamber portions has a rupture member arranged to rupture the respective partition on relative movement of the adjacent chamber portions. Each pair of adjacent chamber portions have respective connection portions mated together, the connection portions being designed to allow further chamber portions identical to an intermediate chamber portion to be connected into said row.

17 Claims, 6 Drawing Sheets

(52) U.S. Cl.
CPC ...... *B01L2200/025* (2013.01); *B01L 2200/028* (2013.01); *B01L 2300/042* (2013.01); *B01L 2300/0672* (2013.01); *B01L 2300/0832* (2013.01); *B01L 2400/0683* (2013.01); *G01N 2001/028* (2013.01)

(56) References Cited

U.S. PATENT DOCUMENTS

| | | | |
|---|---|---|---|
| 4,770,853 A * | 9/1988 | Bernstein | 422/58 |
| 5,116,576 A * | 5/1992 | Stanley | 422/413 |
| 5,137,808 A | 8/1992 | Ullman et al. | |
| 5,188,615 A * | 2/1993 | Haber et al. | 604/203 |
| 5,624,638 A | 4/1997 | Negrotti | |
| 5,905,029 A | 5/1999 | Andreotti et al. | |
| 5,965,453 A | 10/1999 | Skiffington et al. | |
| 6,251,660 B1 * | 6/2001 | Muir et al. | 435/287.2 |
| 6,524,530 B1 | 2/2003 | Igarashi et al. | |
| 6,543,645 B2 * | 4/2003 | Lacout | 222/129 |
| 7,785,535 B2 * | 8/2010 | Chen et al. | 422/82 |
| 2002/0137199 A1 * | 9/2002 | Jobin et al. | 435/287.2 |
| 2002/0197631 A1 * | 12/2002 | Lawrence et al. | 435/6 |
| 2003/0049833 A1 * | 3/2003 | Chen et al. | 435/287.2 |
| 2003/0186458 A1 | 10/2003 | DiCesare et al. | |

FOREIGN PATENT DOCUMENTS

| | | |
|---|---|---|
| EP | 0 859 664 B1 | 3/2003 |
| JP | 5187976 A | 7/1993 |
| JP | H07034370 U | 6/1995 |
| JP | H08505696 A | 6/1996 |
| JP | H11183468 A | 7/1999 |
| JP | 11319029 | 11/1999 |
| JP | H11514849 A | 12/1999 |
| JP | 2001000170 A | 1/2001 |
| WO | WO 92/04978 | 4/1992 |
| WO | WO 95/25948 | 9/1995 |
| WO | WO 97/03209 | 1/1997 |
| WO | WO 97/23596 | 7/1997 |
| WO | WO9723596 * | 7/1997 |
| WO | WO 99/31218 | 6/1999 |
| WO | WO 02/16545 A2 | 2/2002 |
| WO | WO0216545 * | 2/2002 |

OTHER PUBLICATIONS

China Patent Office 1st Office Action regarding Application No. 200580002947.5, mailed Apr. 3, 2009.
China Patent Office 2nd Office Action regarding Application No. 200580002947.5, mailed Oct. 23, 2009.
China Patent Office 3rd Office Action regarding Application No. 200580002947.5, mailed Jul. 29, 2010.
International Preliminary Report on Patentability regarding PCT Application No. PCT/EP2005/000484, dated Aug. 9, 2006.
Japan Patent Office Notice of Reasons for Rejection regarding Application No. 2006-550022, mailed May 20, 2010.
European Office Action regarding Application No. 05 715 193.8 dated Jul. 11, 2012.

* cited by examiner

SAMPLING AND ASSAY DEVICE

TECHNICAL FIELD OF THE INVENTION

The present invention relates to a device for preparation of sample and assay for determination or detection of an analyte, for example by a semi-quantitative or by quantitative inspection apparatus or by semi-quantitative visual inspection of the result and for taking a sample and transportation thereof.

BACKGROUND OF THE INVENTION

For on site testing it is essential to minimise the amount of reagent handling. This can be achieved by using a compact sampling and assay device that contains all the necessary reagents needed for performance of the assay. In many assays, two or more reagents may be used that are combined just prior to, during or after sampling. To fulfil these needs compartmentalised structures with separate reagent reservoirs have been introduced. Several sample preparation and assay devices have been developed for various types of analysis that are aimed for facilitated sampling in both laboratory and non-laboratory environments. Such devices are disclosed for example in U.S. Pat. No. 6,524,530, U.S. Pat. No. 5,905,029, WO-95/25948, WO-99/31218, U.S. Pat. No. 4,770,853, U.S. Pat. No. 4,353,868, WO-97/03209, WO-97/23596 and US-2003/0186458.

All the above mentioned prior art documents disclose sampling and assay devices which comprise the following components: A sampling swab, a tubular container closed from one end, and within this system two or more separate reagent chambers separated by partitions. There are, however, differences in the technical approach of the mechanisms in how the reagents are released and brought into contact with each other and the sample.

A sample collecting member and wiping inspection instrument described in U.S. Pat. No. 6,524,530 is a compact device with a sample wiping member and two partitioned reagents. The sample is first introduced with the extractive reagent in the first container by forcing the swab of the sampling element downward through a seal material. After bacteria adhered to the swab have been extracted the extractive reagent is brought into contact with the reactive reagent by braking the partition of the reagent container by the upward movement of the container relative to the main body of the sampling and assay device. The extracted bacteria flow with the extracting liquid down into the reactive reagent container. In another embodiment of U.S. Pat. No. 6,524,530 a reagent container is upwardly press moved to rupture a seal by the lower end of a breaker followed by a downward movement of the wiping member to rupture the next seal material further followed by a downward movement of the main body to rupture the next seal material by the upper end of the same breaker as above. The document also discloses bacterial detection by a colouring reaction. Moreover, the document discloses that the seal materials are successively tear broken.

U.S. Pat. No. 5,905,029 discloses a method for rapid hygiene testing by detecting ATP in biomass by using a luciferase/luciferin bioluminescent reaction. The document discloses a vial system which uses a series of vials containing necessary reagents and an all-in-one swab device which provides both the swab and the reagents. The luciferace/luciferin may also be isolated in a separate chamber which can be broken to expose the luciferace/luciferin to the buffer solution sealed in another chamber. The buffer solution is released by squeezing the tube.

WO-95/25948 discloses a sample collecting and assay device comprising a tube having a removable top closure on which is mounted an elongate swab. The tube contains one or more reagent compartments separated with frangible membranes. According to the invention two or more compartments can be used, where the base of one compartment may be defined by the top of another. The membranes are successively broken by movement of the swab, or a coaxially-extending blade-like member.

An assay device disclosed in WO-99/31218 comprises a sampling swab and two reagents defined by frangible membranes into separate compartments on top and bottom of the tube. The top reagent may be released by a single operation into the tubular member by relative movement of the two top pieces. The frangible membrane separating the bottom reagent is broken on a movement of the bottom part relative to the tube. The target component in combination with reagents in the compartments undergoes a reaction and gives a detectable signal. The device is suitable for detection of microorganisms obtained by swabbing. The colour produced is visualised through a window and can be compared with a standard. The standard is in the form of reference spots on the device and give a quick indication of the concentration of the analyte in the sample.

U.S. Pat. No. 4,770,853 discloses a compartmentalised sample collecting device with reagent containing sealed chambers and a solid phase immunodiffusion assay area where the presence of the analyte in a sample can be visualised by the naked eye. The device is intended for self contained solid phase immunodiffusion assay which is also based on the breaking of the seals by the sample collector. By an arrangement of nodules and grooves within the test system the contents of a series of independent reagent compartments can be mixed in a stepwise manner.

U.S. Pat. No. 4,353,868 discloses a specimen collecting and transporting device without any analyte determination property. The device includes a swab in a container connected to a closure cap, and a reservoir containing a liquid culture-sustaining medium sealed in a chamber. The seal is broken by the projection of the container when the container is moved relatively toward the reservoir, for example by striking the bottom end wall on some surface, such as a table top and axially or longitudinally move the container relative to the reservoir. The bottom container opening is covered by an absorbent pad which is in contact with the swab tip. When the device is inverted or tilted medium is placed into fluid communication with the absorbent pad allowing controlled or metered flow of the medium through it to the specimen carrying swab tip.

WO-97/03209 describes a test apparatus, system and method for the detection of test samples which includes a probe containing a swab and three compartmentalised reagents within the test unit separated by puncture membranes. The membranes are punctured consecutively by the downward motion of the probe allowing the test sample and the test reagents to react together in the test unit.

US-2003/0186458 discloses an assay device comprising a sampling wand having an internal reservoir which is introduced into a reaction chamber having two portions separated by a frangible seal. Introduction of the sampling wand into the reaction chamber causes rupture of a seal in the sampling wand releasing the reagent in the internal reservoir. Further movement of the sampling wand causes the frangible seal in the reaction chamber to be ruptured allowing the reagent to contact a reactant disc.

Other prior art documents disclose slightly modified solutions from those discussed above. For example a sampling and assay device as described in WO-97/23596 introduces a cap-shaped shuttle that assists the swab in rupturing the partitions between the reagent compartments.

Various purposes of the known devices are to provide an enhanced contact between the sample and the reagent, to determine the analyte in the specimen and, alternatively, to sustain the specimen during transportation. The above-mentioned documents disclose devices where either the swab itself or a rupture member pushed together with the swab is used to rupture the partitions separating the chambers. The design of those penetration means are such that they penetrate the seals in a consecutive order releasing the content of the reservoir into the next one.

There is a need to further improve available assay devices to enhance the test procedure.

SUMMARY OF THE INVENTION

According to a first aspect of the present invention, there is provided a sampling and assay device comprising:

a chamber assembly defining at least three chambers arranged in a row, adjacent chambers along the row being separated by respective partitions, wherein at least one of the chambers is capable of receiving a sample and at least a further two of the chambers contain reagent; and a rupture arrangement capable of rupturing all the partitions simultaneously.

Such a device enables for instance the preparation of the final reagents to be used in an assay. Two or more reagents are partitioned in chambers to avoid their mutual reaction before introduction of the sample to be analysed. In order to accomplish a simultaneous contact between the sample and the two or more available reagents the reservoir members are ruptured simultaneously. In some circumstances it is of importance to have the option to bring two or more reagents together simultaneously just prior to performance of the assay. This is particularly important with reagents which show high or higher stability before combination than after combination. The location of reagents in separate chambers until use provide an excellent stability of the reagents. Consequently, the present invention enables introduction of a high quality reagent on a beforehand defined exact moment. Moreover, the sample collecting and test device of the present invention may be stored for long periods of time, possibly in conditions which usually are not optimal for storage. Thus, the device is suitable for simple and reliable sampling and determination of analyte in the sample, as well as storage prior to use.

In the hereinafter described embodiment, the simultaneous rupture of the partitions is achieved by an arrangement wherein adjacent chamber portions along the row are relatively movable towards each another and, in respect of each pair of adjacent chamber portions, one of the adjacent chamber portions has the respective partition fixed thereto and the other of the adjacent chamber portions has a rupture member arranged to rupture the respective partition on relative movement of the adjacent chamber portions, whereby the sampling and assay device is capable of rupturing all the partitions simultaneously on relative movement of the chamber portions at the ends of the row towards each other.

This arrangement simplifies and further assists the combination of the reagents enclosed in the test device, and obviates the use of a sample element for breaking the partitions.

The device can also be used to transport samples between the site of sampling and the site where the assay is performed. For transportation of samples with special needs of optimal conditions such conditions can be achieved by introducing the sample into a reagent chamber containing reagents maintaining viability of microorganism or inducing and supporting microbial growth or reagents chosen to maintain the proper consistency of the sample.

The partitions may be of any suitable form to prevent leakage of reagent between the chambers. For example, they may be a relatively thin seal or membrane, such as an aluminium foil, formed of a different material from the chamber portions or may be a relatively thick member formed of the same material as the chamber portions. The partitions in the device may be of different configuration, structure or material.

The invention enables a compact configuration of various analyses through its partitioned reagent chamber structure and a rupture arrangement which is simple to use. In addition, the rupture arrangement is not dependent on the sampling element, thus making the device more applicable to various assay and sampling methods, and the means by which the sample is introduced into the device. The device is applicable to various types of sample and reagent since the sampling element is not required in the process of breaking the partitions.

In addition to a normal sampling of surfaces by exploiting a sampler with a swab, a liquid sample can be introduced into the device by means of said swab, pipette, capillary etc. Any kind of visible miniature or larger solid samples suspected to contain the analyte of interest may be introduced into the device by means of for example a tweezers, paddle, spoon or alike. Such solid samples may originate from biological or other material. Samples as biopsies for clinical diagnosis and membranes, filters, food industry and other industry products for hygiene monitoring are of interest. Consequently, the device is suitable for testing any living or non-living material.

As non-limitative examples, possible reagents are labelled or unlabelled antigens, labelled or unlabelled binding substances such as antibodies, anti-antibodies and antigens and their analogues, hemolytic agents, agents separating blood and serum/plasma, agglutinating compounds as a lectin etc. Moreover, the reagent may comprise both single and dual size labelled or unlabelled particles as latex, gold, liposomes etc. The reagents may be, for example, in fluid, non-fluid, freeze-dry or lyophilised form. Furthermore the reagents may include any chemicals useful for the assay or which may participate in the reaction.

The device may rely on semi-quantitative or quantitative determination of analyte and is especially suitable for out-of-laboratory testing. It may rely on an inspection apparatus which may be portable apparatus. The use of the test device is not limited to instrumental detection means but is also suitable for semi-quantitative visual inspection.

The chamber portions may serve as reagent chambers, and/or a monitoring cuvette. This enables the sampling and assay device to be applicable to semi-quantitative and to quantitative measurement because of the reaction chamber structure and material compatible with both the approaches. When semi-quantitative determinations are needed usually a visual inspection is adequate enough. For quantitative inspections analyzers suitable for quantitative assays are needed. Usually optical measurement techniques as absorbance, extinction, turbidimetry, nephelometry, reflectance, fluorescence, phosphorescence, luminescence and others are preferred.

In a first type of embodiment, the chamber portion at one end of the row is a tubular body having an open end distal from the adjacent chamber portion in the row for insertion of a swab for carrying a sample.

In a second type of embodiment, the chamber portion at one end of the row has a cap which is removable to allow entry of a sample to the chamber.

Advantageously, the sampling and assay device further comprises a barrier element extending across the chamber of the one of the chamber portions which has the partition fixed thereto to prevent passage of the ruptured partition. This prevents the ruptured partition, which may become detached in part or in full from passing into the adjacent chamber where it might prevent proper mixing of the reagents or prevent proper inspection of the analyte. The barrier element is sufficiently open to allow passage of any desired reagent or sample into the reaction reservoir.

Advantageously, the sampling and assay device further comprises a removable blocking element arranged between a pair of adjacent chamber portions to prevent relative movement between the pair of adjacent chamber portions. Each partition is protected from unintentional rupture by the blocking element which prevents the relative movement between the pair of adjacent chamber portions. The removable blocking element may be formed integrally with one of the chamber portions for example as a tear strip. If such a removable blocking element is provided between each pair of adjacent chamber portions it also enables a sequential assay procedure, by removing the blocking elements one by one in an order determined by the need of any given time.

According to a second aspect of the present invention, there is provided a system for assembling sampling and assay devices having a plurality of chambers arranged in a row, the system comprising:

at least one type of end chamber portion defining a chamber and having a connection portion;

at least one type of intermediate chamber portion defining a chamber and having two connection portions, wherein the connection portions of the types of end chamber portion and intermediate chamber portion are capable of being mated together to assemble a sampling and assay device with an end chamber portion, at least one intermediate chamber portion and a further end chamber portion connected in a row.

Such a system allows straightforward production of a variety of different sampling and assay devices having different reagents by assembly of the chamber portions.

In a system preferred for its simplicity, there is a type of intermediate chamber portion each have a first and second connection portions, the first connection portion of one intermediate chamber portion being capable of being mated to the second connection portion of a another intermediate chamber portion. As a result of this arrangement of the connection portions, any number of intermediate chamber portions of this type can be connected directly together.

To allow better understanding, embodiments of the present invention will now be described, by way of non-limitative example with reference to the drawings.

DETAILED DESCRIPTION OF THE DRAWINGS

Figure 1:
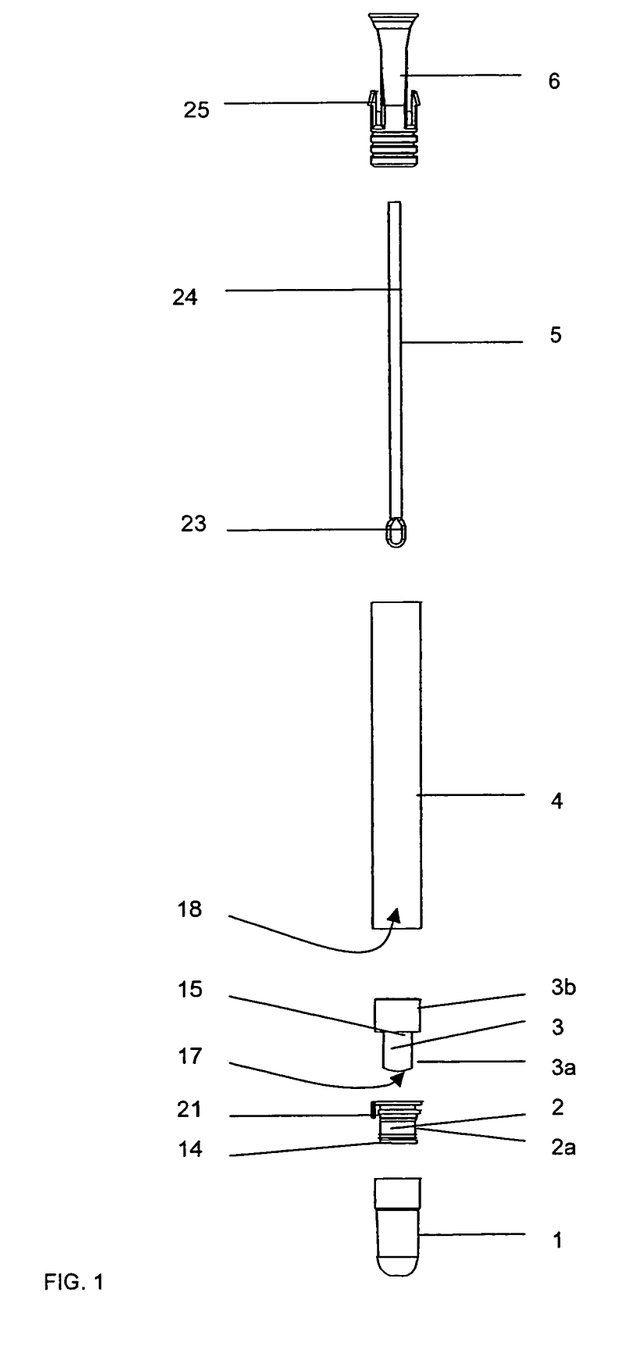
FIG. 1 is an exploded view of a sampling and assay device with three chambers which is a first embodiment of the invention.

FIG. 1 is an exploded view of the invention showing a reaction chamber portion 1; a sealing cap 2 with a sealing partition 14 and a tear strip 21; a reagent chamber portion 3 with an intermediate solid partition 15 and a rupture member 17; an outermost tubular body 4; a sampling element 5 with a swab 23 and a shaft 24; and a holder 6 with catch 25.

Figure 2:
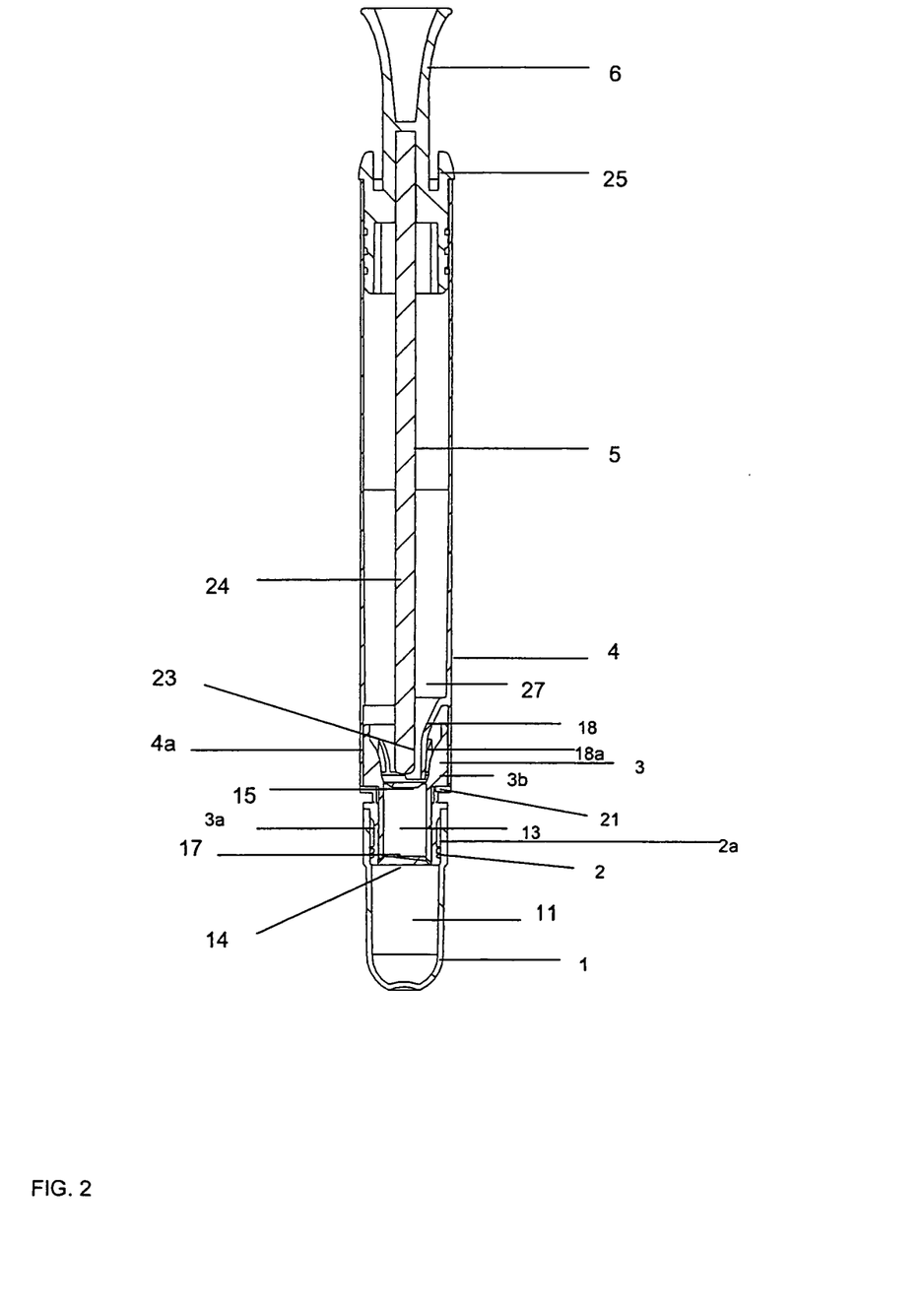
FIG. 2 is an enlarged cross sectional view of the device presented in FIG. 1.

FIG. 2 is a cross sectional view of the invention showing a reaction chamber portion 1; a sealing cap 2 with a sealing partition 14 and a tear strip 21; a reagent chamber portion 3 with an intermediate solid partition 15 and a rupture member 17; an outermost tubular body 4 with an elongate inner wall 18; a sampling element 5 with a swab 23 and a shaft 24; and a holder 6 with catch 25.

Figure 3:
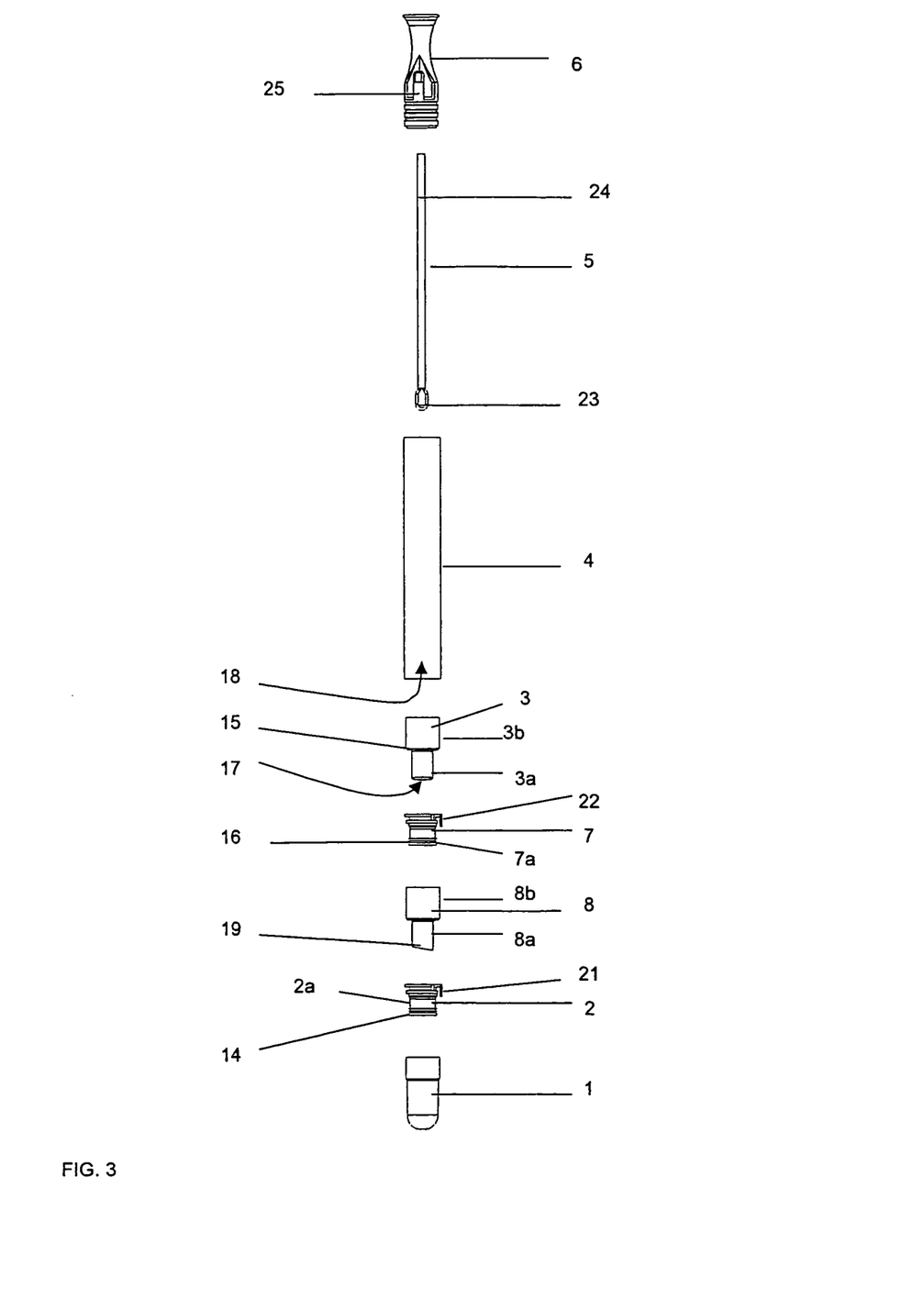
FIG. 3 is an exploded view of a sampling and assay device with four chambers which is a second embodiment of the invention.

FIG. 3 is an exploded view of the invention showing a reaction chamber portion 1; a first sealing cap 7 with a sealing partition 16 and a tear strip 22; an additional chamber portion 8 with a rupture member 19; a second sealing cap 2 with a sealing partition 14 and a tear strip 21; a reagent chamber portion 3 with an intermediate sealing partition 15 and a rupture member 17; an outermost tubular body 4 with an elongate inner wall 18; a sampling element 5 with a swab 23 and a shaft 24; and a holder 6 with catch 25.

Figure 4:
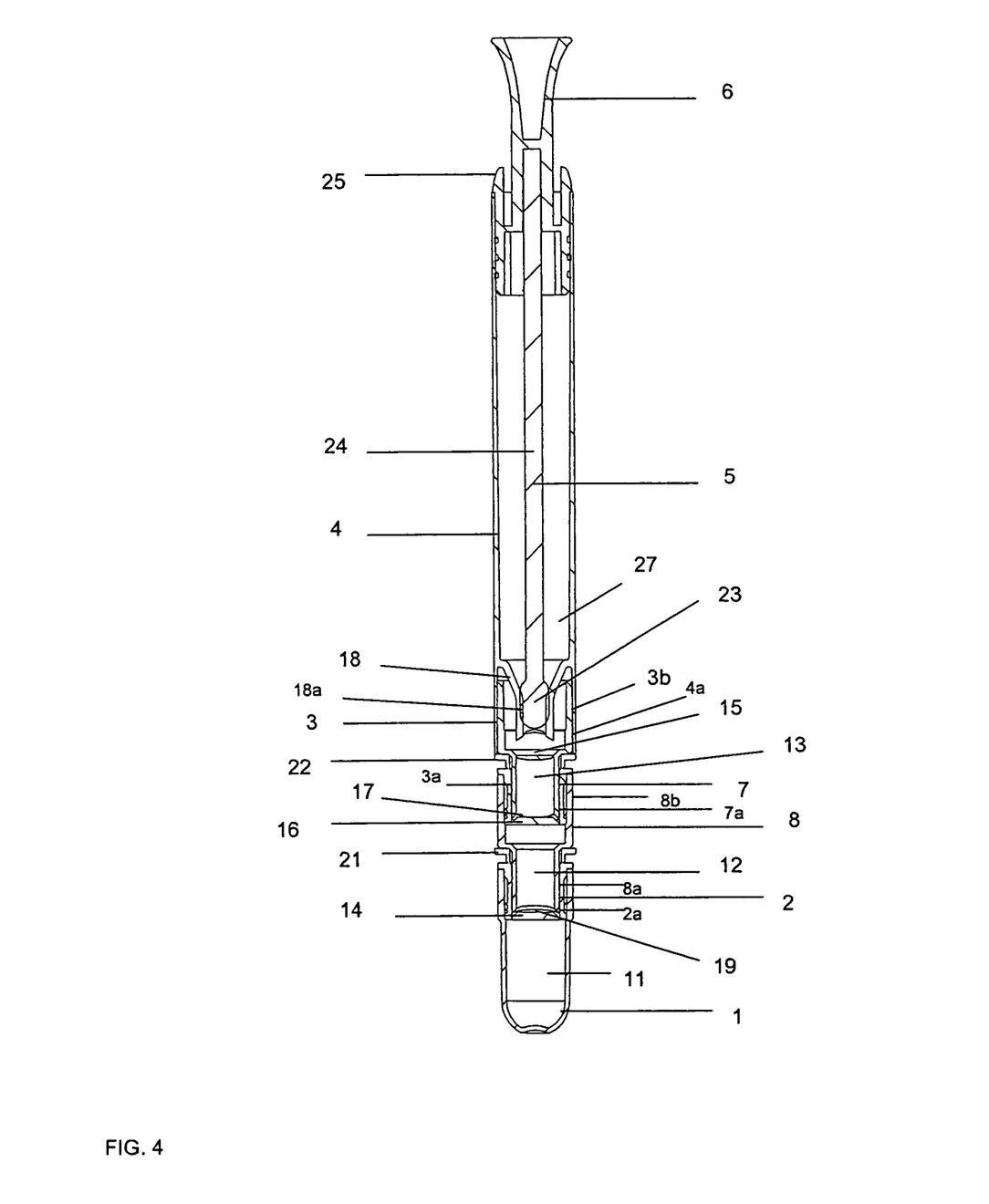
FIG. 4 is an enlarged cross sectional view of the device presented in FIG. 3.

FIG. 4 is a cross sectional view of the invention showing a reaction chamber portion 1; a sealing cap 2 with a sealing partition 14 and a tear strip 21; an additional chamber portion 8 with a rupture member 19; an additional sealing cap 7 with a sealing partition 16 and a tear strip 22; a reagent chamber portion 3 with an intermediate sealing partition 15 and a rupture member 17; an outermost tubular body 4 with an elongate inner wall 8; a sampling element 5 with a swab 23 and a shaft 24; a holder 6 with catch 25; and two reagent reservoirs 12, 13.

Figure 5:
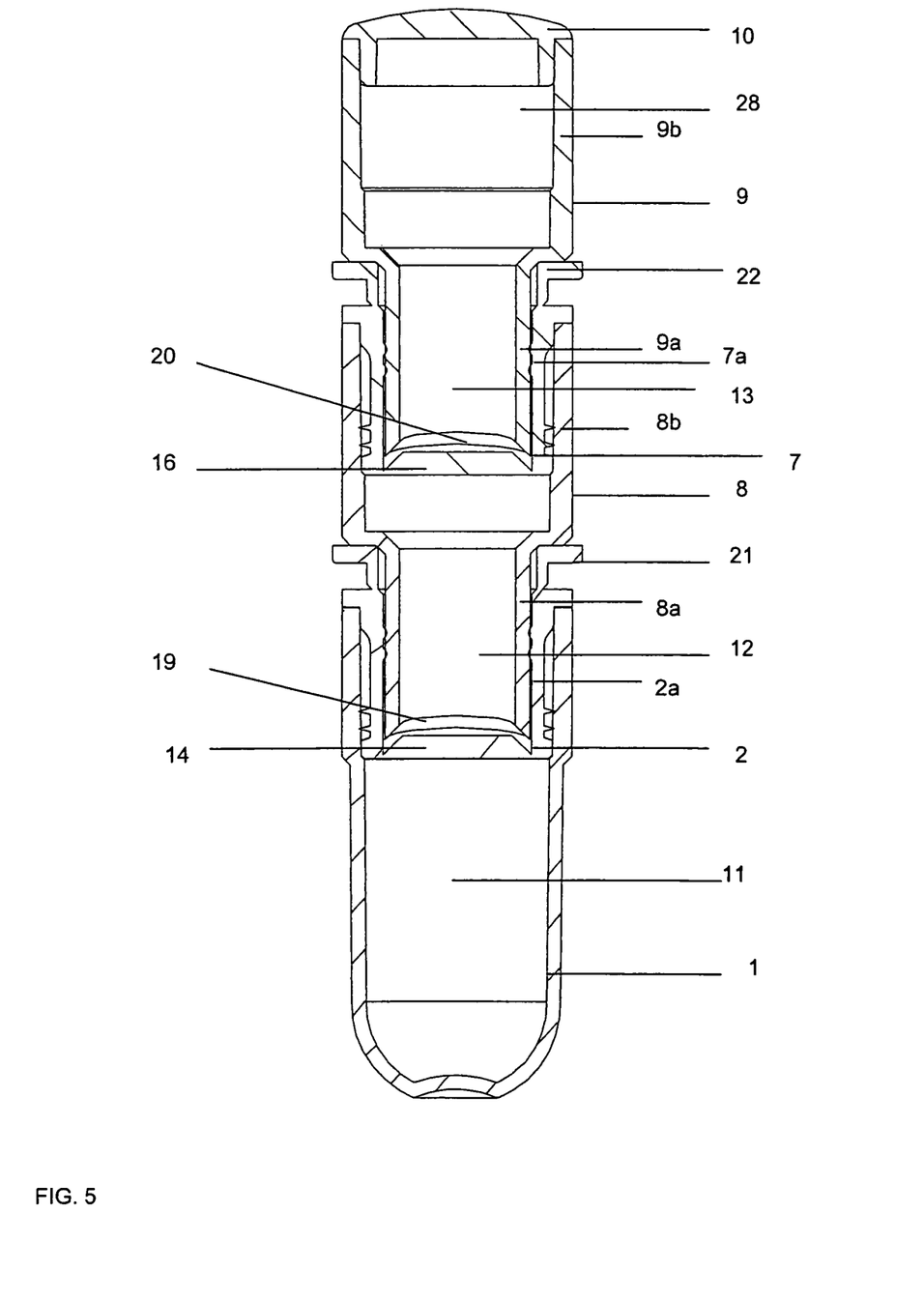
FIG. 5 is an enlarged cross sectional view of the invention with three chambers which is a third embodiment of the invention.

FIG. 5 is a cross sectional view of the invention showing a reaction chamber portion 1; two reagent reservoirs 12,13 comprising a sealing cap 2 with a sealing partition 14 and a tear strip 21, and an additional chamber portion 8 with a rupture member 19; an additional sealing cap 7 with a sealing partition 16 and a tear strip 22, and a sample chamber portion 9 with a sharp edge 20; and a closing cap 10.

Figure 6:
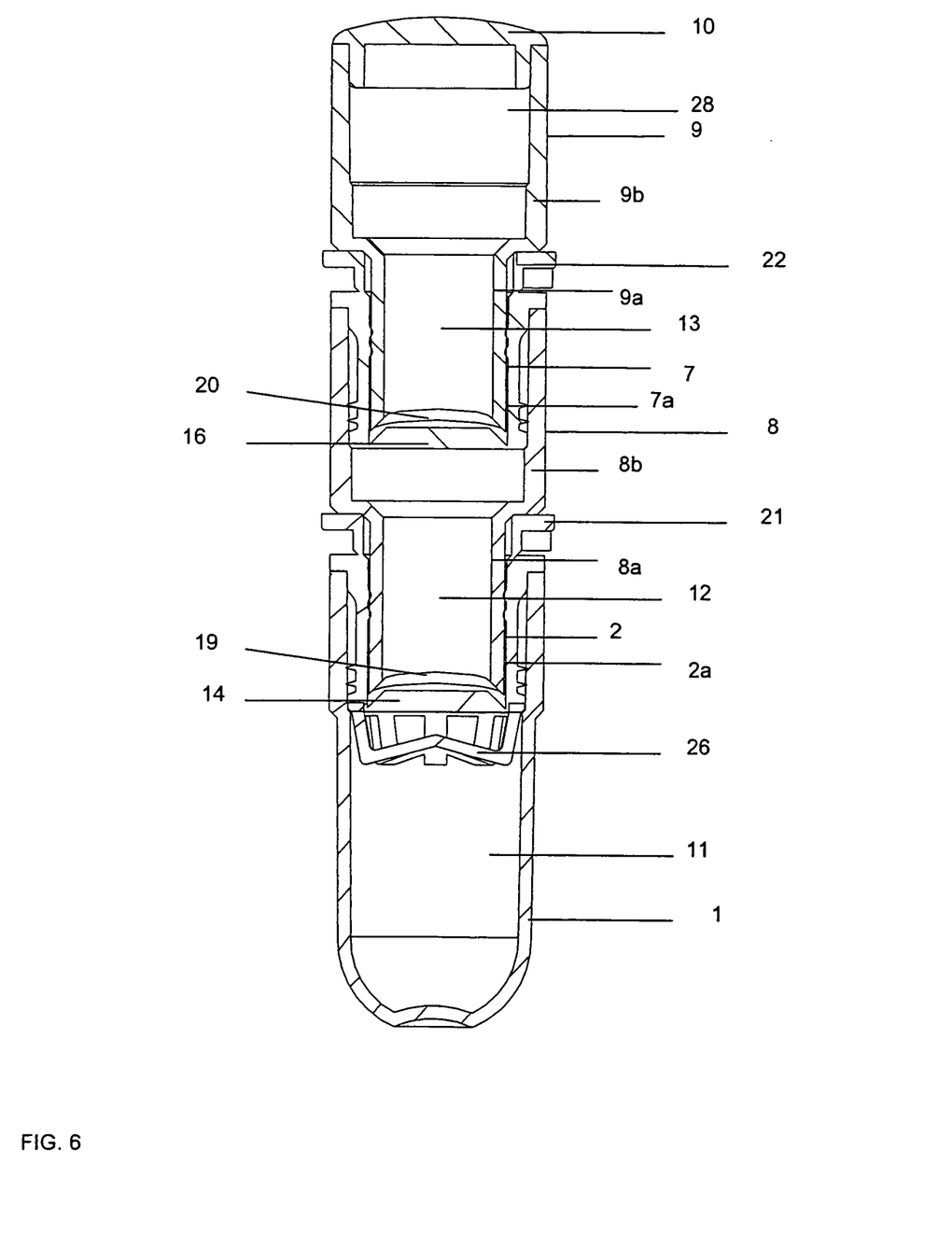
FIG. 6 is a cross sectional view of the invention with three chambers and a barrier element which is a fourth embodiment of the invention.

FIG. 6 is a cross sectional view of the invention showing the reaction chamber portion 1 with a barrier element 26; two reagent reservoirs 12,13 comprising a sealing cap 2 with a sealing partition 14 and a tear strip 21, and an additional chamber portion 8 with a rupture member 19; an additional sealing cap 7 with a sealing partition 16 and a tear strip 22, and a sample chamber portion 9 with a rupture member 20; and a stopper 10.

DETAILED DESCRIPTION OF THE INVENTION

FIGS. 1. and 2 illustrate a sampling and assay device comprising a test tube shape reaction chamber portion 1 in the form of an annular body defining a chamber 11 that may serve as a reagent reservoir, reaction chamber and/or a monitoring cuvette for visual inspection or for a measurement by an automatic reader designed for example for turbidimetric or nephelometric assays.

The reaction chamber portion 1 has an opening at one end sealed with a sealing cap 2 having an annular wall 2a fitting in the opening of the reaction chamber portion 1. The annular wall 2a forms a female connection portion by which the reaction chamber portion 1 is connected to a reagent chamber portion or body 3 which also defines a chamber 13.

The sealing cap 2 has, extending across the aperture at the innermost end of the annular wall 2a which forms a female connection portion, a partition 14 formed integrally with the annular wall 2a, which separates the chambers 11, 13 defined by the reaction chamber portion 1 and the reagent chamber portion 3.

The reagent chamber portion 3 comprises (a) a first annular portion 3a serving as a male connection portion mating with the female connection portion 2a of the sealing cap 2 with friction contact to prevent leakage of fluid or other reagents, and (b) a second annular portion 3b protruding from the first annular portion 3a and having a larger diameter than the first annular portion 3a, serving as a male connection portion mating with a tubular body 4 which defines a chamber 27 for receipt of a sample. Optionally, the chamber 27 of the tubular body 4 may contain a buffer which may be a solution for maintaining the sample prior to performance of the assay or for facilitating the reaction process.

The reagent chamber portion 3 has a partition 15 formed integrally across the aperture in the second annular portion 3b of the reagent chamber portion 3 to separate the chambers 13, 27 defined by the reagent chamber portion 3 and the tubular body 4. Thus, the chamber 13 of the reagent chamber portion 3 is bounded by the partition 14 of the sealing cap 2 and the partition 15 of the reagent chamber portion 3. The reaction chamber portion 1, the reagent chamber portion 3 and the tubular body 4 (which may be considered as a further chamber portion) are arranged in a row with the reagent chamber portion 3 intermediate the reaction chamber portion 1 and the tubular body 4 at opposite ends of the row. The chambers 11, 13 defined by the reaction chamber portion 1 and the reagent chamber portion 3 both contain a respective reagent. The chamber 13 of the reagent chamber portion 3 may be used as a reservoir for a reagent and/or as a reaction chamber.

The reaction chamber portion 1 and the reagent chamber portion 3 are relatively movable towards one another from the position shown in FIG. 1 by the male connection portion 3a sliding inside the female connection portion 2a. The edge 17 of the male connection portion 3a of the reagent chamber portion 3 facing the partition 14 is sharp and pointed so as to serve as a rupture member 17 capable of puncturing the partition 14 of the sealing cap 2 on movement of the reaction chamber portion 1 and the reagent chamber portion 3 towards one another.

The sealing cap 2 has a tear strip 21 integrally attached around the end of the female connection portion 2a. The tear strip 21 serves as a blocking element which engages the second annular portion 3b of the reagent chamber portion 3 and thus prevents movement of the reaction chamber portion 1 and the reagent chamber portion 3 towards one another. This in turn prevents unintentional breaking of the partition 14 by the sharp edge 17 of the male connection portion 3a of the reagent chamber portion 3. In use, the partition 14 is ruptured by relative movement of the reaction chamber portion 1 and the reagent chamber portion 3 once the tear strip 21 has been removed by detaching it from the sealing cap 2. Puncturing of the partition 14 allows the reagents contained in the reaction chamber portion 1 and the reagent chamber portion 3 to mix.

The tubular body 4 defines a chamber 27 having an open end through which a sampling element 5 may be removably inserted. The sampling element 5 consists of a blade shape swab 23 and a shaft 24. The sample is taken by contacting the swab 23 with the sample material. Depending on the sample material the shaft 24 may be either rigid or flexible.

The tubular body 4 is connected to the reagent chamber portion 3 by an annular skirt 4a which forms a female connection portion mated with the male connection portion 3b of the reagent chamber portion 3.

The tubular body 4 and the reagent chamber portion 3 are relatively movable towards one another from the position shown in FIG. 1 by the male connection portion 3b sliding inside the female connection portion formed by the annular skirt 4a. Inside the annular skirt 4a, the tubular body 4 has a wall 18 extending around an internal aperture of sufficient size to allow insertion and passage of the swab 23. The end of the wall 18 facing the partition 15 is sharp and pointed so as to serve as a rupture member 18a capable of puncturing the partition 15 of the reagent chamber portion 3 on movement of the tubular body 4 and the reagent chamber portion 3 towards one another.

The tear strip 21 also serves as a blocking element which engages the end of the annular skirt 4a of the tubular body 4 and thus prevents movement of the tubular body 4 and the reagent chamber portion 3 towards one another. This in turn prevents unintentional breaking of the partition 15 by the rupture member 18a of the tubular body 4. In use, the partition 15 is ruptured by relative movement of the tubular body 4 and the reagent chamber portion 3 once the tear strip 21 has been removed by detaching it from the sealing cap 2.

According to the present invention, when the tubular body 4 and the reaction chamber portion 1 are relatively moved towards one another, there is simultaneously relative movement between the tubular body 4 and the reagent chamber portion 3 and relative movement between the reaction chamber portion 1 and the reagent chamber portion 3. As a result, the partition 14 and the partition 15 are simultaneously ruptured. To facilitate simultaneous rupture, it is desirable that the gaps between the partition 14 and the rupture member 17 and between the partition 15 and the rupture member 18a are relatively small preferably at most 3 mm, more preferably at most 1 mm.

A holder 6 is attached to the sampling element 5. The holder 6 is equipped with catch 25 that serves as an engagement portion for engaging open end of the tubular body 4. The catch 25 holds the sampling element 5 with the swab 23 inside the wall 18 at a position separated from the partition 15 and outside the chamber 13 defined by the reagent chamber portion 3. Thus the catch 25 prevents the swab 23 from unintentionally moving downward and thus entering the area of partition 15 where it could disrupt the partition 15. In this position, the swab 23 is protected by the wall 18 from damage by the partition 15 after rupture.

The catch 25 is deflectable inwardly to release the open end of the tubular body 4 and thereby allow the sampling element to be inserted further into the tubular body 4. In use, the catch 25 is released and the swab 23 is moved through the chamber 13 defined by the reagent chamber portion 3 into the reaction chamber 11 after rupture of the partitions 14 and 15. This brings the sample on the swab 23 into contact with the reagents which are now mixed.

FIGS. 3 and 4 illustrate a second sampling and assay device which is identical to the first sampling and assay device shown in FIGS. 1 and 2 except for the inclusion of an additional chamber portion or body 8. For brevity, the common components will be given the same reference numerals and a description thereof will not be repeated.

The additional chamber portion 8 is arranged between the reaction chamber portion 1 and the reagent chamber portion 3 and defines a chamber 12 containing a reagent.

The additional chamber portion 8 comprises (a) an annular body 8b, and (b) an annular portion 8a protruding from the annular body 8b with a smaller diameter than the annular body 8b, serving as a male connection portion mating with the female connection portion 2a of the sealing cap 2 with friction contact to prevent leakage of fluid or other reagents. The additional chamber portion 8 lacks an intermediate partition and differs in that respect from that of reagent chamber portion 3.

The annular portion 8a of the additional chamber portion 8 is identical to the male connection portion 3a of the reagent chamber portion 3. Thus, the reaction chamber portion 1 and the additional chamber portion 8 are relatively movable towards one another from the position shown in FIG. 4 by the male connection portion 8a sliding inside the female connection portion 2a. Similarly, the edge of the male connection portion 8a of the additional chamber portion 8 facing the partition 14 is sharp and pointed so as to serve as a rupture member 19 capable of puncturing the partition 14 of the sealing cap 2 on movement of the reaction chamber portion 1 and the additional chamber portion 8 towards one another. The tear strip 21 performs the same function as in the first sampling and assay device but for relative movement of the reaction chamber portion and the additional chamber portion 8.

The annular body 8b of the additional chamber portion 8 is identical to the part of the reaction chamber portion 1 around its opening and has an opening at one end sealed with an additional sealing cap 7 which is identical to the sealing cap 2. Thus the additional sealing cap has an annular wall 7a fitting in the opening of the additional chamber portion 8. The annular wall 7a forms a female connection portion by which the additional chamber portion 8 is connected to the reagent chamber portion 3.

The additional sealing cap 7 has, extending across the aperture at the innermost end of the annular wall 7a which forms a female connection portion, a partition 16 formed integrally with the annular wall 7a, which separates the chambers 12, 13 defined by the additional chamber portion 8 and the reagent chamber portion 3. Thus, the chamber 12 of the additional chamber portion 8 is bounded by the partition 14 of the sealing cap 2 and the partition 16 of the additional sealing cap 7. The reaction chamber portion 1, the additional chamber portion 8, the reagent chamber portion 3 and the tubular body 4 (which may be considered as a further chamber portion) are arranged in a row with the reagent chamber portion 3 and the additional chamber portion 8 intermediate the reaction chamber portion 1 and the tubular body 4 at opposite ends of the row.

The additional sealing cap 7 has a tear strip 22 which is identical to the tear strip 21 of the first sampling and assay device and performs the same function except with respect to relative movement between the additional chamber portion 8 and the reagent chamber portion 3

The second sampling and assay device may be used in the same manner as the first sampling and assay device by first removing both the tear strips 21 and 22. This allows the tubular body 4 and the reaction chamber portion 1 to be relatively moved towards one another, which causes simultaneously relative movement between (1) the tubular body 4 and the reagent chamber portion 3, (2) the reagent chamber portion 3 and the additional chamber portion 8 and (3) the additional chamber portion 8 and the reaction chamber portion 1. As a result, all the partitions 14, 15 and 16 are simultaneously ruptured.

Alternatively, the tear strips 21 and 22 may be sequentially removed allowing sequential rupture of the partitions 14, 15, and 16. This allows the reagents to be mixed in any desired order according to the order in which the tear strips are removed.

Also, the nature of the connection portions 8a and 8b of the additional chamber portion 8 is such that any number of further additional chamber portions 8 could be introduced into the device intermediate the reaction chamber portion 1 and the reagent chamber portion 3. This is a significant advantage and provides a system allowing a variety of different sampling and assay devices containing different reagents to be assembled.

FIG. 5 illustrates a third sampling and assay device which is identical to the second sampling and assay device shown in FIGS. 3 and 4 except that the reagent chamber portion 3 and tubular body 4 are replaced by a sample chamber portion 9. For brevity, the components which are common with the first or second sampling and assay devices will be given the same reference numerals and a description thereof will not be repeated.

The sample chamber portion 9 has an identical construction to the additional chamber portion 8. Thus, the sample chamber portion 8 comprises (a) an annular body 9b, and (b) an annular portion 9a protruding from the annular body 9b with a smaller diameter than the annular body 9b, serving as a male connection portion mating with the female connection portion 7a of the sealing cap 7 with friction contact to prevent leakage of fluid or other reagents. The annular portion 9a of the sample chamber portion 9 is identical to the male connection portion 8a of the reagent chamber portion 8. Thus, the sample chamber portion 9 and the additional chamber portion 8 are relatively movable towards one another from the position shown in FIG. 5 by the male connection portion 9a sliding inside the female connection portion 7a. Similarly, the edge of the male connection portion 9a of the sample chamber portion 9 facing the partition 16 is sharp and pointed so as to serve as a rupture member 20 capable of puncturing the partition 16 of the sealing cap 7 on movement of the sample chamber portion 9 and the additional chamber portion 8 towards one another. The tear strip 21 performs the same function as in the first sampling and assay device but for relative movement of the sample chamber portion 9 and the additional chamber portion 8.

The sample chamber portion 9 defines a chamber 28 for receiving a solid or liquid sample. The annular body 9b of the additional chamber portion 9 is identical to the part of the reaction chamber portion 1 around its opening and has an opening at one end sealed with a stopper 10 which is removable to allow insertion of a sample into the chamber 28 defined by the sample chamber portion 9. Thus the chamber 28 defined by the sample chamber portion 9 is bounded by the stopper 10 and the partition 16. Optionally, the chamber 28 of the sample chamber portion 9 may contain a reagent. Alternatively, the chamber 28 of the sample chamber portion 9 may contain a buffer which may be a solution for maintaining the sample prior to performance of the assay or for facilitating the reaction process.

In use, first the stopper 10 is removed, the sample which may be in any phase is inserted into the chamber 28 of the sample chamber portion 9 and the stopper 10 is replaced. Subsequently the third sampling and assay device is used in the same manner as the second sampling and assay device by removing the tear strips 21 and 22 and moving the reaction chamber portion 1 and the sample chamber portion 10 towards each other to rupture the partitions 14 and 16. As before, the partitions 14 and 16 may be ruptured simultaneously or sequentially controlled by the sequence of removal of the tear strips 21 and 22.

As an alternative, the additional chamber portion 8 may be omitted, so that the sample chamber portion 9 is connected directly to the reaction chamber portion 1.

FIG. 6 illustrates a fourth sampling and assay device which is identical to the third sampling and assay device shown in FIG. 5 except that the sealing cap 2 has an integrally formed barrier element 26 extending across the chamber 11 of the reaction chamber portion 1 on the opposite side of the partition 14 from the rupture member 19. The barrier element 26 prevents passage of the ruptured partition 14, but has openings to allow passage of reagent therethrough. Instead of being integrally formed with the sealing cap 2, the barrier element 26 may be integrally formed with the reaction chamber portion 1 or may be a separate element mounted to the reaction chamber portion 1 or sealing cap 2.

Examples of the use of the sampling and assay devices described above will now be described.

If the device is intended for monitoring the clinical health or the disease of a patient by determining analytes in the field of clinical chemistry and infectious diseases, usually quantitative or qualitative immunological assays are performed. Generally, either an antibody or antigen concentration is measured from biological fluids, excreta or tissue fluids (such as blood, sera, plasma, spinal fluid, pleural exudate, ascites, pus, wound suppuration, urine, sputum, faeces, pharyngeal smear sample etc.). The test may be direct, indirect or inhibitory by the nature. In immunological assays an antigen specific antibody binds to said antigen. Prior to the assay the binding substance, either the antibody or alternatively anti-antibody or the antigen may be bound to a specific labelling indicator (marker). Such a marker is selected from the group of i.e., polymeric particles (including dyed and magnetic particles), colloidal gold, stained substrates, fluorescent and phosphorescent molecules and luminescent molecules. All the above mentioned reagents, including buffer and washing reagents, may be enclosed in advance into the chambers of the device. Furthermore, the reagent reservoirs may contain adsorbants, anticoagulants, buffers, diluents, dye solutions, extraction reagents, inactivators, labelled or unlabelled antibodies their fragments or analogues, labelled or unlabelled antigens, medium, etc. which mix with the sample. The reagents in the chambers may be in fluid form or alternatively freeze-dried or lyophilised in order to achieve an even longer storage at non-refrigerated temperatures.

In the following descriptions, the device and the method will be described in exemplary terms only, for measurement of reducing agent and Group A Streptococci antigen. The device can be used for a variety of other analysis involving two or more reagents combined with a sample. The disclosure below illustrates the structure and use of the device.

Example 1

The first device of FIGS. 1 and 2 is suitable for detection of reducing agents, including proteins and reducing sugars e.g. glucose, fructose, lactose and maltose. The sample, indicative of surface cleanliness/dirtiness, is taken by wiping a surface with a sampling element 5 initially placed inside the tubular body 4 of the device. The sampling element 5 is inserted back inside the tubular body 4, and the tear strip 21 between the sealing cap 2 and the reagent chamber portion 3 is removed. There is copper reagent (4% aqueous $CuSO_4.5H_2O$) in the chamber 13 defined by the reagent chamber portion 3, and organic acid reagent (4% organic acid, sodium carbonate and bicarbonate, and sodium tartrate in 0.1 M NaOH) in the chamber 11 defined by the reaction chamber portion 1. These reagents are combined by relative movement of the reaction chamber portion 1 and the tubular body 4. By this movement the rupture member 17 of the reagent chamber portion 3 and the rupture element 18a of the tubular body 4 rupture the partitions 14 and 15. Once the partitions 14 and 15 between the chambers 11, 13, 27 have been broken, the sampling element 5 has a free passage into the chamber 11 defined by the reaction chamber portion 1. The sample absorbed into the swab 23 is brought into contact with the combined reagents in the reaction chamber portion 1 by squeezing the catch 25 of the holder 6 and by inserting the sampling element into the reaction chamber portion 1 where the colour reaction indicative of the reducing agent concentration takes place.

Example 2

The second device of FIGS. 3 and 4 is suitable for Group A Streptococci (*Streptococcus pyogenes*) detection and measurement by Quik Read photometric reader (Orion Diagnostica, Finland). The sample is taken by wiping the pharyngeal cavity with a sampling element 5 initially placed inside the tubular body 4 of the device. The sampling element 5 is inserted back inside the tubular body 4, and the tear strip 22 between the additional sealing cap 7 and the reagent chamber portion 3 is removed. There is a first extraction reagent (0.02% phenol red in 3 M $NaNO_2$) in the chamber 13 defined by the reagent chamber portion 3 and the tubular body 4 and a second extraction reagent (0.005 M EDTA in 1 M acetic acid) in the chamber 12 defined by the additional chamber portion 8. These reagents are combined relative movement of the additional chamber portion 8. By this movement the rupture member 17 of the reagent chamber portion 3 and the rupture member 18 of the tubular body 4 rupture the partitions 15 and 16. Once the partitions 15 and 16 have been broken, the sampling element 5 has a free passage through the chamber 13 into the chamber 11 where the sample is extracted for 3 minutes. After the extraction, the tear strip 21 between the sealing cap 2 and the additional chamber portion 8 is removed, and the extract is combined with the reagent buffer (0.095% NaCl in 0.2 M, 0.9% Tris-$NaN_3$, pH 8.4) in the reaction chamber portion 1 by a movement of the reaction chamber portion 1 relative to the outermost tubular body 4. Once the reagents are combined, the reaction chamber portion 1 can be disconnected from the sampling element 5, the additional chamber portion 8, and the reagent chamber portion 3, together with the tubular body 4, by pulling off the compact pack outlined by the sealing cap 2, the outermost tubular body 4 and the holder 6. The extracted sample in the reagent buffer is now introduced with freeze dried Group A Streptococci antibody coated latex particles, for example by using a separate closure device as described in EP-0,859,664 or alike. The closure device is placed inside the reaction chamber portion 1, and the latex particles are released into the reagent buffer by pushing the plunger of the closure device downward. The sample in the reagent buffer and the antibody coated latex particles, in the reaction chamber portion 1, are mixed with a vigorous shaking, after which the mixture is incubated for a few minutes. The reaction response is measured as turbidity against blank sample by inserting the reaction chamber portion 1, sealed with the closure device, inside the photometric reader Quik Read (Orion Diagnostica, Finland).

LIST OF ELEMENTS IN THE DRAWINGS

1 Reaction chamber portion
2 Sealing cap
2a Annular wall of sealing cap 2 serving as a female connection portion
3 Reagent chamber portion
3a First annular portion of reagent chamber portion 3 serving as a male connection portion
3b Second annular portion of reagent chamber portion 3 serving as a male connection portion
4 Tubular body
4a Annular skirt of the tubular body 4
5 Sampling element
6 Holder
7 Sealing cap, identical to sealing cap 2
7a Annular wall of sealing cap 7
8 Additional chamber portion
8a Annular portion of additional chamber portion 8 serving as a male connection portion
8b Annular body of additional chamber portion 8
9 Sample chamber portion, identical to additional chamber portion 8
9a Annular portion of additional chamber portion 9 serving as a male connection portion
9b Annular body of additional chamber portion 9
10 Stopper
11 Chamber defined by the reaction chamber portion 1
12 Chamber defined by the additional chamber portion 8
13 Chamber defined by the reagent chamber portion 3
14 Sealing partition of the sealing cap 2
15 Sealing partition of the reagent chamber portion 3
16 Sealing partition of the sealing cap 7
17 Rupture member of the reagent chamber portion 3.
18 Wall of the tubular body 4
18a Rupture member of the tubular body 4
19 Rupture member of the additional chamber portion 8
20 Rupture member of the sample chamber portion 9
21 Tear strip of the sealing cap 2
22 Tear strip of the sealing cap 7
23 Swab of the sampling element 5
24 Shaft of the sampling element 5
25 Catch of the holder 6
26 Barrier element
27 Chamber of tubular body 4
28 Chamber of sample chamber portion 9

The invention claimed is:

1. A sampling and assay device comprising:
a first body having a first rupture member;
a second body slidably connected to the first body and including a first sealing partition and a second rupture member, the second body defining a first chamber;
a third body slidably receiving the second body and a second sealing partition, the first and second sealing partitions sealing opposing ends of the first chamber, the third body including a third rupture member and defining a second chamber; and
a fourth body slidably receiving the third body and a third sealing partition, the second and third sealing partitions sealing opposing ends of the second chamber, the fourth body defining a third chamber that is sealed by the third sealing partition,
wherein the first chamber is at least partially disposed between the first sealing partition and the second rupture member, and
wherein the second chamber is at least partially disposed between the second sealing partition and the third rupture member.

2. The sampling and assay device of claim 1, further comprising a sampling element releasably engaged with the first body.

3. The sampling and assay device of claim 2, wherein the sampling element includes a swab that is receivable within an aperture extending through the first rupture member.

4. The sampling and assay device of claim 3, wherein the swab is mounted to a holder having a releasable engagement portion arranged, on insertion of the swab into an opening of the first body, to engage the first body with the swab held outside the first chamber and, on release, to allow insertion of the swab into the first chamber.

5. The sampling and assay device of claim 4, wherein the releasable engagement portion comprises a catch arranged to engage the opening of the first body and being deflectable to release the opening of the first body.

6. The sampling and assay device of claim 1, wherein the fourth body includes a closed end.

7. The sampling and assay device of claim 1, wherein the second sealing partition is in a sealing cap that receives a portion of the second body.

8. The sampling and assay device of claim 1, wherein the third sealing partition is in a sealing cap that receives a portion of the third body.

9. The sampling and assay device of claim 1, further comprising a barrier element extending across the third chamber.

10. The sampling and assay device of claim 1, further comprising a removable blocking element arranged between the second body and the third body to prevent relative movement between the second and third bodies.

11. The sampling and assay device of claim 10, wherein the blocking element includes an annular ring surrounding the second body and disposed axially between an axial end of the first body and an axial end of the third body.

12. The sampling and assay device of claim 10, wherein the blocking element is a tear strip.

13. The sampling and assay device of claim 1, further comprising a removable blocking element arranged between the third body and the fourth body to prevent relative movement between the third and fourth bodies.

14. The sampling and assay device of claim 13, wherein the blocking element includes an annular ring surrounding the third body and disposed axially between an axial end of the fourth body and an annular ledge of the third body.

15. The sampling and assay device of claim 13, wherein the blocking element is a tear strip.

16. The sampling and assay device of claim 1, wherein an axial end of the first body has an annular skirt that receives the second body.

17. The sampling and assay device of claim 1, wherein at least one of the first and fourth bodies is optically transparent in at least a part thereof for inspection of the contents.

* * * * *